(12) United States Patent
Brichard et al.

(10) Patent No.: US 11,284,803 B2
(45) Date of Patent: Mar. 29, 2022

(54) LOW CAPACITANCE ENDOSCOPIC SYSTEM

(71) Applicant: INTUITIVE SURGICAL OPERATIONS, INC., Sunnyvale, CA (US)

(72) Inventors: Dominique Brichard, San Jose, CA (US); Peter M. Herzlinger, Saratoga, CA (US); David D. Scott, Oakland, CA (US); Klaus Zietlow, Piedmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 848 days.

(21) Appl. No.: 14/080,384

(22) Filed: Nov. 14, 2013

(65) Prior Publication Data
US 2014/0155758 A1    Jun. 5, 2014

Related U.S. Application Data

(60) Provisional application No. 61/726,879, filed on Nov. 15, 2012.

(51) Int. Cl.
*A61B 5/02* (2006.01)
*A61B 1/00* (2006.01)
(Continued)

(52) U.S. Cl.
CPC ............ *A61B 5/02* (2013.01); *A61B 1/00004* (2013.01); *A61B 1/0008* (2013.01);
(Continued)

(58) Field of Classification Search
CPC ............ A61B 1/00004; A61B 1/00018; A61B 1/0008; A61B 5/02; A61B 5/6847; A61B 34/30; A61B 2505/05; A61B 2562/182
See application file for complete search history.

(56) References Cited

U.S. PATENT DOCUMENTS 3,690,313 A * 9/1972 Weppner ................. G01R 19/18
                                                            600/508
4,106,494 A * 8/1978 McEachern .......... A61N 1/3931
                                                            600/508
(Continued)

FOREIGN PATENT DOCUMENTS

CN        1204243 A      1/1999
CN     102258359 A     11/2011
(Continued)

OTHER PUBLICATIONS

Blyth, "Converters Address Medical Equipment Compliance", Power Electronics Technology, Mar. 2006, pp. 38-41.*
(Continued)

*Primary Examiner* — Colin T. Sakamoto
(74) *Attorney, Agent, or Firm* — Jones Robb, PLLC

(57) ABSTRACT

An endoscopic system can include an endoscope shaft having a proximal end and a distal end, and an electrically active sensor system including at least one sensor mounted proximate the distal end and positioned to sense at least one characteristic of an environment in which the distal end is located. The capacitance of the sensor system relative to earth ground maintains current leakage to a level that meets a cardiac float rating.

20 Claims, 7 Drawing Sheets

(51) Int. Cl.
*A61B 5/00* (2006.01)
*A61B 34/30* (2016.01)

(52) U.S. Cl.
CPC ........ *A61B 1/00018* (2013.01); *A61B 5/6847* (2013.01); *A61B 34/30* (2016.02); *A61B 2505/05* (2013.01); *A61B 2562/182* (2013.01)

(56) References Cited

U.S. PATENT DOCUMENTS

| | | | |
|---|---|---|---|
| 4,607,621 | A | 8/1986 | Wheeler |
| 5,309,918 | A * | 5/1994 | Schraag ................ A61B 5/301 600/508 |
| 5,569,158 | A | 10/1996 | Suzuki et al. |
| 5,716,323 | A | 2/1998 | Lee |
| 5,810,714 | A | 9/1998 | Takamura et al. |
| 5,825,259 | A | 10/1998 | Harpham |
| 5,873,816 | A | 2/1999 | Kagawa et al. |
| 5,913,817 | A | 6/1999 | Lee |
| 6,319,197 | B1 | 11/2001 | Tsuji et al. |
| 7,132,819 | B1 | 11/2006 | Cope et al. |
| 9,993,135 | B2 | 6/2018 | Brichard et al. |
| 2009/0018429 | A1 * | 1/2009 | Saliga ................ A61B 5/7221 600/407 |
| 2010/0261961 | A1 | 10/2010 | Scott et al. |
| 2010/0286477 | A1 | 11/2010 | Ouyang et al. |
| 2011/0018988 | A1 | 1/2011 | Kazakevich et al. |
| 2011/0152879 | A1 | 6/2011 | Williams |
| 2011/0282358 | A1 | 11/2011 | Gomez et al. |
| 2011/0292194 | A1 | 12/2011 | Kato |
| 2014/0135579 | A1 | 5/2014 | Brichard et al. |
| 2014/0167518 | A1 * | 6/2014 | Risher-Kelly .......... H02M 1/44 307/89 |
| 2015/0263673 | A1 * | 9/2015 | Biel ...................... A61B 5/252 600/372 |
| 2018/0102739 | A1 * | 4/2018 | Biel ................... H03F 3/45076 |

FOREIGN PATENT DOCUMENTS

| | | |
|---|---|---|
| EP | 1862108 A2 | 12/2007 |
| EP | 2161967 A1 | 3/2010 |
| EP | 2430972 A1 | 3/2012 |
| JP | H08126213 A | 5/1996 |
| JP | H10135681 A | 5/1998 |
| JP | H10305009 A | 11/1998 |
| JP | 2000279381 A | 10/2000 |
| JP | 2003126029 A | 5/2003 |
| JP | 2004202040 A | 7/2004 |
| JP | 2009045113 A | 3/2009 |
| WO | WO-2011120014 A1 | 9/2011 |
| WO | WO-2014078538 A1 | 5/2014 |

OTHER PUBLICATIONS

Lee, "Isolated RS485 Transceiver Breaks Ground Loops—Design Note 228", Linear Technology, 2000.*
Linear Technology "LTC1535: Isolated RS485 Transceiver" datasheet published 2009.*
International Search Report and Written Opinion for Application No. PCT/US2013/070102, dated Feb. 13, 2014, 16 pages.
Partial Supplementary European Search Report for Application No. 13855377.1, dated May 30, 2016, 6 pages.
"National Deviations to IEC 60601-1", MDDI Medical Device and Diagnostic Industry News Products and Suppliers, Feb. 1, 2004, pp. 1-4. Retrieved from the Internet: http://www.mddionline.com/article/national-deviations-iec-60601-1.
Extended European Search Report for Application No. 13855377.1, dated Sep. 28, 2016, 11 pages.
Office Action dated Jan. 4, 2017 for Chinese Application No. 201380059277.5 filed Nov. 14, 2013, 25 pages.
Office Action dated Oct. 1, 2018 for European Application No. 13855377.1 filed Nov. 14, 2013, 3 pages.

* cited by examiner

LOW CAPACITANCE ENDOSCOPIC SYSTEM

CROSS-REFERENCE TO RELATED APPLICATIONS

This application claims priority to U.S. Provisional Application No. 61/726,879, filed Nov. 15, 2012, which is incorporated by reference in its entirety herein.

TECHNICAL FIELD

The present disclosure is generally directed to endoscopic systems. More particularly, aspects of the present disclosure relate to endoscopic systems that include electrically active components disposed at an applied part of the system.

INTRODUCTION

Minimally invasive surgical techniques generally attempt to perform surgical procedures while minimizing damage to healthy tissue. Remotely-controlled instruments, which can include robotically-controlled (teleoperated) or manually-controlled instruments, can be used to perform various minimally invasive procedures remotely. In robotically-controlled (teleoperated) surgical systems, surgeons manipulate various input devices at a surgeon console (sometimes referred to herein as master inputs) to control one or more corresponding remotely-controlled instruments at a remote site in a patient's body. The input at the surgeon console is communicated to a patient side cart that interfaces with one or more teleoperated surgical instruments, where teleoperated/telerobotic manipulation of the surgical instrument occurs to perform a surgical and/or other procedure on the patient.

Minimally invasive surgical instruments may be used in a variety of operations and have various configurations. Many such instruments include a surgical end effector mounted at a distal end of a long shaft that is configured to be inserted (e.g., laporoscopically or thoracoscopically) through an opening (e.g., body wall incision or natural orifice) to reach a remote surgical site within a patient. In some instruments, an articulating wrist mechanism is mounted to the distal end of the instrument's shaft to support the end effector and alter an orientation (e.g., pitch and/or yaw) of the end effector with reference to the shaft's longitudinal axis. Teleoperated/telerobotically controlled end effectors may be configured to perform various functions, including any of a variety of surgical procedures that are conventionally performed in either open or manual minimally invasive surgical procedures.

The use of remotely-controlled, minimally invasive surgical instruments, whether teleoperated or manually-controlled, generally is aided by an endoscopic image capture system to capture real-time images from the surgical site and provide the captured images to, for example, the surgeon console or elsewhere for access by a user. In a teleoperated surgical system, such an endoscopic system also can be mounted at the patient side cart. Such a system can include, among other elements, a shaft (either flexible or rigid), an image capture device at the proximal end of the endoscopic system, such as, for example, a camera, a light conductor (such as one or more fiber optics or a rod lens) that can provide images of the surgical site once the shaft is in position proximate the surgical site to the image capture device at the proximal end, and a light source for illuminating the surgical site.

Portions of minimally invasive surgical instruments and/or tools that may contact the patient during their normal operation (sometimes referred to as "applied parts"), and that are electrically active (e.g., require electrical power to operate), can cause an electrical current exceeding an allowable leakage current for the part to flow to earth or to a conductive part of the overall instrument, tool, or system that the instrument or tool is a part of. Therefore, these parts may need to be isolated from, for example, one or more earth-grounded elements of the associated surgical system in order to reduce the risk of electric shock to the patient. In particular, depending on the nature of the applied part and the type of contact the applied part may make with the patient, the applied part may fall into one of several classification ratings, for example, as set by the International Electrotechnical Commission (IEC) in the IEC 60601-1 safety standard. For example, an applied part that may come in direct contact with a patient's heart may be required to meet at least the IEC 60601-1 Cardiac Float ("CF") rating, while an applied part that may come in direct contact with the patient, but not with the patient's heart, may be required to meet at least the IEC 60601-1 Body Float ("BF") rating, which is less stringent than the CF rating. In light of various electrically active components employed in, for example, endoscopic image capture systems, such endoscopic systems may require their applied parts to be isolated from, for example, external/earth-grounded power supplies.

Further, the applied part of an endoscopic system may exchange output and/or control signals with an electronic circuit, for example, at the patient side cart, at the surgeon console, and/or at an electronics/auxiliary control cart. In some cases, however, it may be desirable to use an endoscopic system in the presence of electromagnetic interference (EMI) at the remote site in the patient. For example, electrocautery operations, in which tissue at a surgical site is subject to application of cautery energy generated by the flow of electrical current through an electrocautery instrument, require application of a relatively high amount of electrical current through a conducting element in close proximity to other instruments at the remote site.

A need exists to provide endoscopic systems that use electrically active sensor systems to capture and provide information from a remote surgical site that are sufficiently electrically isolated in their applied parts. For example, it may be desirable to provide an endoscopic system that meets the requirements of a desired standard rating with regard to protection from electrical shock, such as, for example, an IEC CF rating.

A need also exists to provide endoscopic systems that use electrically active sensor systems to capture and provide information from a remote surgical site that are sufficiently shielded so as to result in acceptably low levels of noise interference occurring from EMI at the remote site.

It also may be desirable to provide an endoscopic system that can achieve both sufficiently low capacitance and current leakage (e.g., to achieve an IEC CF rating) and also is sufficiently shielded to result in acceptably low levels of EMI noise interference, for example, from cautery procedures and/or other relatively high EMI generation at the remote site.

SUMMARY

The present disclosure solves one or more of the above-mentioned problems and/or demonstrates one or more of the above-mentioned desirable features. Other features and/or advantages may become apparent from the description that follows.

In accordance with at least one exemplary embodiment, the present disclosure contemplates an endoscopic system that can include an endoscope shaft having a proximal end and a distal end, and an electrically active sensor system including at least one sensor mounted proximate the distal end and positioned to sense at least one characteristic of an environment in which the distal end is located. The capacitance of the sensor system relative to earth ground maintains current leakage to a level that meets a cardiac float rating.

In accordance with at least another exemplary embodiment, the present disclosure contemplates a method for sensing information at a remote surgical site via an endoscopic system. The method can include, at a remote surgical site, sensing a characteristic of the remote surgical site via a sensor disposed proximate a distal end of an endoscope shaft. During the sensing, power can be transmitted to the sensor via a power transmission line from a ground-referenced power source, and data signals can be transmitted to the sensor via a data signal transmission line from a processing circuit at a proximate end of the endoscopic shaft. In response to electromagnetic interference proximate the remote surgical site, the method further can include substantially equalizing induced voltages level changes in the data signal transmission line and the power transmission. The method can further include maintaining current leakage from one or more applied parts of the endoscopic system at a sufficiently low level to meet requirements of a cardiac float rating.

Additional objects and advantages will be set forth in part in the description that follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the invention, as disclosed or claimed. The claims should be entitled to their full breadth of scope, including equivalents.

BRIEF DESCRIPTION OF THE DRAWINGS

The present disclosure can be understood from the following detailed description either alone or together with the accompanying drawings. The drawings are included to provide a further understanding of the present disclosure, and are incorporated in and constitute a part of this specification. The drawings, which are incorporated in and constitute a part of this specification, illustrate one or more embodiments of the present disclosure and, together with the description, serve to explain certain principles and operation. In the drawings.

DETAILED DESCRIPTION

Figure 1:
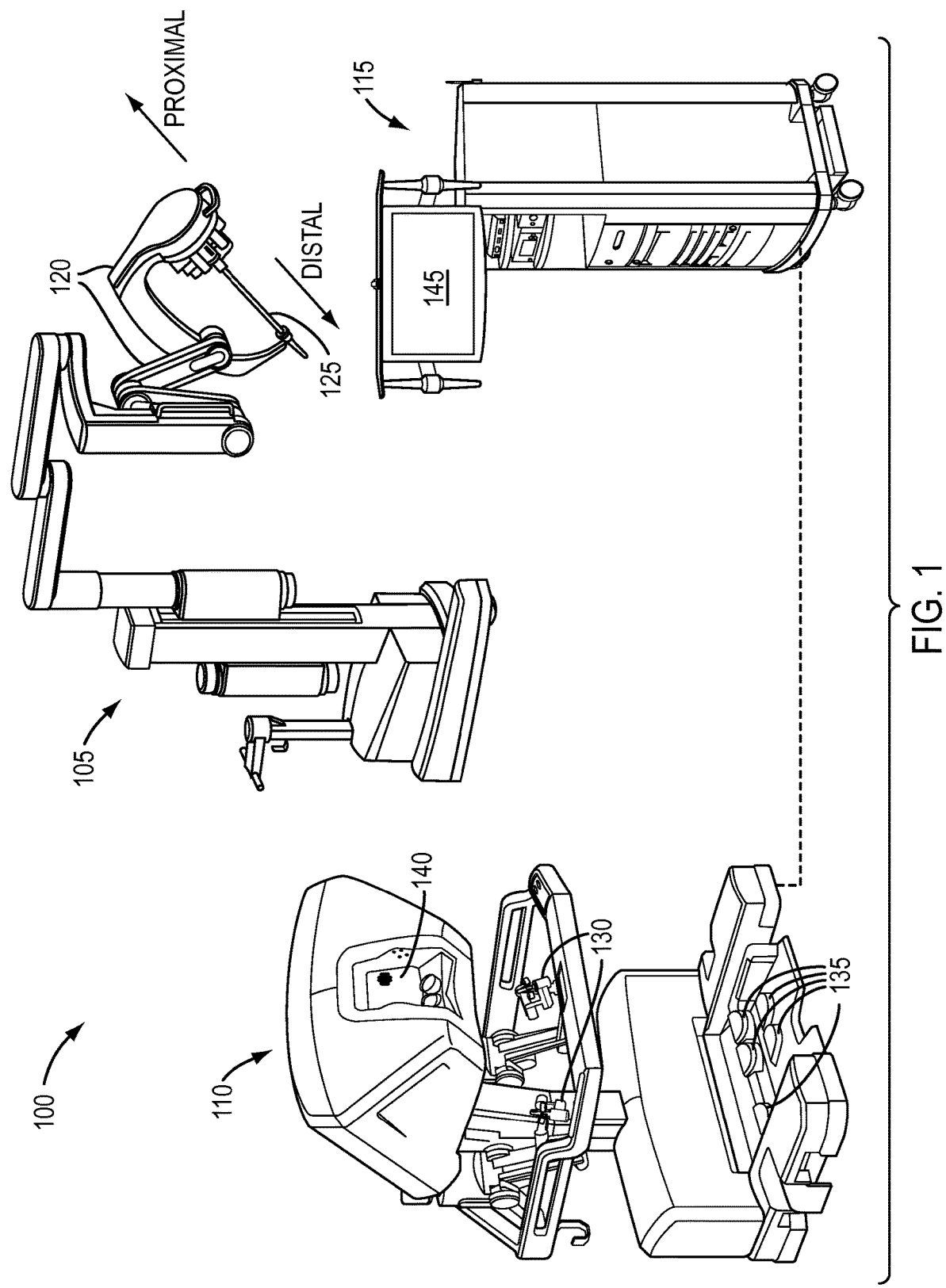
FIG. 1 is a diagrammatic view of an exemplary embodiment of a minimally invasive teleoperated surgical system in which the present disclosure may be applied.

This description and the accompanying drawings illustrate exemplary embodiments and should not be taken as limiting, with the claims defining the scope of the present disclosure, including equivalents. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or the electrosurgical instrument.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Although the exemplary embodiments and descriptions below focus mainly on an endoscopic system including an endoscopic distally positioned image sensor for capturing images of a remote surgical site, the principles of the present disclosure can be applied in other endoscopic systems, such as, for example, that utilize one or more electrically active components at an applied part (e.g., in a distal portion of the endoscope shaft). For example, aside from having image sensor systems, endoscopic systems in accordance with the present disclosure can include any of a variety of electrically active sensor systems for providing one or more characteristics of a remote site. Examples of such endoscopic sensor systems can include, but are not limited to, ultrasonic endoscopic probe systems, pressure transducer systems (e.g., for measuring arterial blood pressure), electromagnetic sensor systems (e.g., for positioning and/or steering), temperature sensor systems, etc. Moreover, those having ordinary skill in the art would understand that the present teachings can be applied in non-surgical applications wherein it may be desirable to utilize a remotely-navigable instrument that utilizes one or more electrically active components (e.g., sensors) to capture and provide information at a remote site, and that may benefit from the isolation and/or EMI noise interference shielding configurations described herein, such as industrial sensing applications and/or location sensing and tracking applications.

As used herein, a "sensor system" and variations thereof includes not only the sensor mechanism itself (e.g., temperature probe, image capture device, transducer, etc.) but also the circuitry, wiring, and other ancillary structure, including both electrically active and electrically passive components, that enable the sensor to sense, convert, and transmit data and power from or to a surgical site to be used by an operator of the device and/or stored remotely from the surgical site as those of ordinary skill in the art are familiar with.

Some conventional teleoperated surgical systems include electrically passive endoscopic systems in which no electrically active elements are present at the distal end of the endoscopic shaft of the endoscopic system. In such systems, light is transferred through the endoscopic shaft through passive elements such as, for example, one or more optical fibers or a rod lens, and an electrically active image sensor/camera captures light/images from the passive elements at the proximal end of the endoscopic system. With such a lack of electrically active applied parts, sufficiently low capacitance and leakage currents between the applied part and patient tissue can be achieved via a relatively simple mechanical insulation barrier.

Other endoscopic systems may rely on an applied part at the distal end of the endoscopic shaft of the endoscopic system that includes an electrically active element. The use of the electrically active element and its system components may require the applied part to include some level of electrical isolation from earth ground (e.g., a low capacitance of the applied part to earth ground) to achieve, for example, at least a BF rating. Although the electrically active element may be fully or partially exposed to patient tissue, in exemplary embodiments the electrically active element is configured and positioned relative to the applied part such that its electrical isolation from earth ground is that of the applied part. An electrically active element, and associated signal/power transmission lines along the endoscopic shaft (e.g., a sensor system), may however be susceptible to EMI if used in the presence of EMI-generating surgical instruments such as, for example, an electrocautery surgical instrument. EMI levels may be exacerbated as the applied part's capacitance to earth ground is lowered. This is because interfering voltage imposed on the associated signal/power transmission lines by such EMI may increase as the capacitance of the applied part to earth ground decreases. In other words, while interference with the associated signal/power transmission lines can be reduced by providing a low-impedance (e.g., high capacitance) path between the applied part containing the electrically active element and earth ground, such relatively high capacitance may cause a relatively high leakage current between the applied part and patient tissue, which may thereby prevent the endoscopic system from meeting requirements to achieve a desired rating for protection against electrical shock (e.g., whether a BF or CF rating), and thus, from being used for certain surgical procedures.

Various exemplary embodiments of the present disclosure provide endoscopic systems having relatively low capacitance between an electrically active element at an applied part and patient tissue. In particular, various exemplary embodiments include, for example, an optical communication link between circuitry at the proximal end of the endoscopic system and the associated robotically-controlled surgical system, in combination with other elements of the endoscopic system to isolate a floating circuit which includes the electrically active element from the ground reference of the patient tissue and to reduce the capacitance between the electrically active element and its associated signal transmission lines, circuitry, etc., and patient tissue.

Furthermore, various exemplary embodiments of the present disclosure provide endoscopic systems that shield an electrically active element and other components from EMI. In particular, various exemplary embodiments include tight coupling of the induced voltage experienced by signal and power transmission lines between the electrically active element and circuitry at the proximal end of the endoscopic system, a high capacitance between the signal/power transmission lines and the floating ground of a floating circuit which includes the electrically active element and the circuitry at the proximal end of the endoscopic system, and a continuous shielding element for shielding the floating circuit.

Further still, various exemplary embodiments of the present disclosure provide an endoscopic system having relatively low capacitance between an electrically active element at an applied part and earth ground and that shield the electrically active element and other components from EMI. Exemplary embodiments also provide endoscopic systems which may achieve a CF rating while being capable of protecting against noise interference resulting from operating in the presence of other surgical instruments that may generate relatively high levels of EMI. Thus, by achieving a CF rating, various exemplary embodiments provide an endoscopic system that may be employed for a variety of procedures, including procedures in the caridiothoracic cavity and heart.

With reference to FIG. 1, a diagrammatic view of an exemplary embodiment of a minimally invasive teleoperated surgical system 100 in which the present disclosure may be applied is depicted, although those of ordinary skill in the art will recognize that the principles herein can be applied in manual minimally invasive surgical systems as well. Teleoperated surgical system 100 includes a patient side cart 105, a surgeon console 110, and an electronics/auxiliary control cart 115. It is noted that the system components in FIG. 1 are not shown in any particular positioning and can be arranged as desired, with patient side cart 105 being disposed relative to the patient so as to affect surgery on the patient. A non-limiting, exemplary embodiment of a teleoperated surgical system that shares the general master-slave robotic control principles of operation as those contemplated herein is a da Vinci® Si (model no. IS3000) commercialized by Intuitive Surgical, Inc. of Sunnyvale, Calif., although those of ordinary skill in the art would understand that the present disclosure is not in any way limited to that particular system.

Surgical system 100 is used to perform minimally invasive remote surgical procedures by interfacing with and controlling a variety of surgical instruments. The patient side cart 105 can include a patient side manipulator arm 120 for holding, positioning, and manipulating the various surgical instruments and/or associated tools. As shown in FIG. 1, the arm 120 of patient side cart 105 is configured to interface with and control one or more remotely-controlled surgical instruments and/or endoscopes (a single general instrument/ endoscope 125 being depicted diagrammatically for simplicity in FIG. 1).

In operation, surgeon console 110 receives inputs from a surgeon by various input devices, including but not limited to, for example, one or more master grip input mechanisms 130 and/or one or more foot pedals 135. Through the input devices, such as, for example the grip input mechanisms 130, the surgeon console 110 serves as a master controller by which one or more instruments mounted at the patient side cart 105 act as a slave to implement any desired motions of the surgical instrument(s) (e.g., including their end effectors), and accordingly perform a desired surgical procedure. Other input commands also may be provided at the surgeon side console 110 to control various functionalities of instruments mounted at the patient side cart 105. By way of non-limiting example, a foot pedal 135 may be depressed to send a cautery command to deliver electrosurgical energy from an electrosurgical instrument mounted at the patient side cart 105. However, robotic surgical system 100 is not limited to receiving inputs at the surgeon console 110, and inputs may be received at any device which can be configured to realize a manipulation of the surgical instrument(s) at the patient side cart 105. For example, a surgical instrument at the patient side cart 105 may be manipulated by a user (e.g., a surgeon) at the patient side cart 105, through the surgeon console 110 in combination with other surgical instrument support device, or entirely through another surgical support device, as a result of inputs received from the user. In addition, input devices can have a variety of configurations other than gripping mechanisms or foot pedals. Such configurations can include, but are not limited to, for example, joysticks, kinetic sensors, switches, thumb/finger controls, etc.

Surgeon console 110 may further include an electronic data processing system, including a processor, which may be configured to receive and process inputs from the surgeon console 110, or from any other surgical instrument support device, and control the manipulation of one or more surgical instruments at the patient side cart 105 based on such inputs. However, elements of such electronic data processing system may be provided elsewhere within robotic surgical system 100.

Electronics/auxiliary control cart 115 receives and transmits various control signals to and from the patient side cart 105 and the surgeon console 110, and can transmit light and/or other processing signals (for example, to and from an endoscopic system mounted at the patient side cart 105). For example, image processing light and image capture command signals can be provided from the electronics/auxiliary control cart 115, for example, in response to master command inputs provided at the surgeon console 110, for capturing and processing images via an endoscopic imaging system mounted at the patient side cart 105. The captured images may be displayed at a display 140 at the surgeon console 110 and/or on a display 145 associated with the electronics/auxiliary control console 115. Other electronics to control functionality of the various surgical instruments, such as electrosurgical energy generation units, for example, also may be located at the electronics/auxiliary control cart 115. Those having ordinary skill in the art are generally familiar with such electronics/auxiliary control carts of remotely-controlled robotic surgical systems.

In various exemplary embodiments, a camera control mechanism may be used to send signals to an endoscopic camera manipulator ("ECM") embedded at the arm 120, and to an endoscopic camera, to control various aspects related to capturing and processing video of a surgical site, such as the position/orientation of the camera with respect to the surgical site, zoom of the camera lens, focus of the camera lens, etc. Those having ordinary skill in the art are generally familiar with the use of such teleoperated/telerobotic surgical systems to provide input from a surgeon at a surgeon console to ultimately effect operation of a surgical instrument interfacing with a patient side cart.

Figure 2:
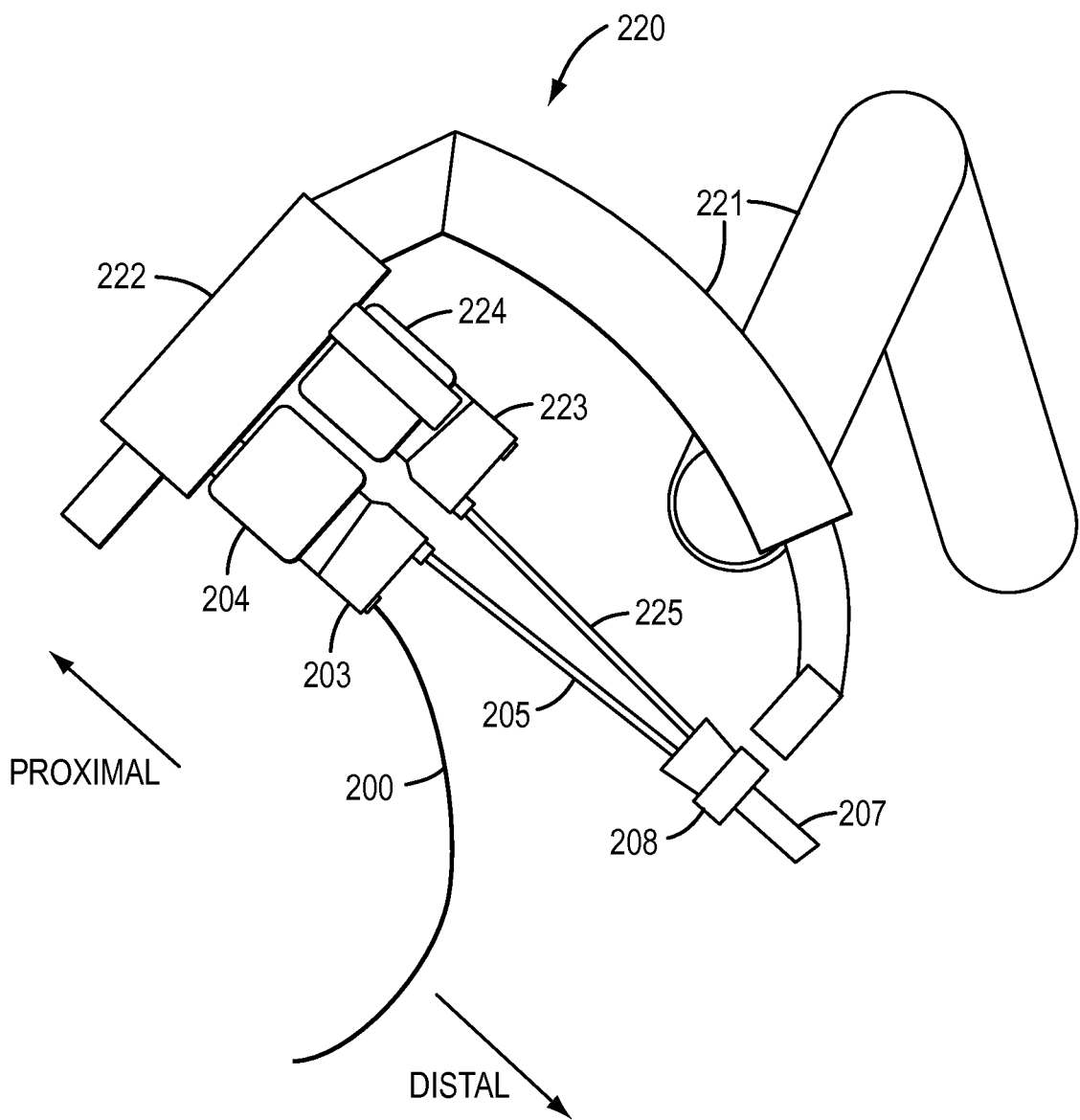
FIG. 2 is a diagrammatic perspective view of a portion of a patient side manipulator arm of a minimally invasive teleoperated surgical system in accordance with at least one exemplary embodiment of the present disclosure.

FIG. 2 illustrates a side elevation view of a patient side manipulator arm 220 with an illustrative endoscopic camera 205 and an additional surgical instrument 225 mounted thereto according to an exemplary embodiment of the present disclosure. In the exemplary embodiment, the patient side manipulator arm 220 includes a "set-up" portion (not shown in FIG. 2) (which generally is passive and not controlled by the surgeon console) and an actively controlled "manipulator" portion 221, 222. The portion 222 supports individual manipulator/actuator assemblies 204, 224 (for simplicity, only two manipulator assemblies are illustrated, one associated with the endoscopic camera (i.e., ECM) and one with the surgical instrument). The manipulator portion 222 can include a rotatable base that rotates all of the manipulator assemblies and mounted instruments together about an arbitrarily defined roll axis. The manipulator assemblies 204, 224 engage with transmission housings 203, 223 associated with the endoscope camera instrument 205 and the surgical instrument 225, respectively, to control movement of instruments 205, 225. In exemplary embodiments, not shown in FIG. 2, the distal portions of the instrument shafts have wrist mechanisms that can be articulated (e.g., in arbitrary pitch and/or yaw) and rolled in response to actuators the manipulator portions 204 that transmit various forces through the transmission housings 203, 223. The distal portions of the mounted instruments 205, 225 are received through an entry guide structure 208 that may lead to a cannula 207 that is introduced into the patient's body at a single incision site or "port." Although not depicted in FIG. 2, the distal end portions of the instruments can exit out of the distal end of the cannula 207 (or other access structure) to access the remote surgical site.

The directions "proximal" and "distal" are used herein to define relative locations of elements of surgical instruments/ devices, with distal generally being in a direction further along a kinematic chain, which can include a surgical instrument or endoscope camera, or closest to the surgical work site in the intended operational use of the associated instrument used for performing surgical procedures. FIG. 2 indicates the proximal and distal directions. For a further description of an exemplary patient side cart for mounting and motion control of surgical and endoscopic instruments that can be utilized with the present disclosure, reference is made to U.S. App. Pub. No. US 2011/0282358 A1, published Nov. 17, 2011, which is incorporated by reference in its entirety herein. A camera manipulator portion according to an exemplary embodiment may include more or less elements than those described with reference to FIG. 2. For example, a camera arm according to the present disclosure may include more, less, or none of the motion actuators set forth in FIG. 2 without departing from the scope of the present disclosure. Further, as noted above, the present disclosure is not limited to an endoscopic image capture sensor or camera, and an endoscopic system according to the present teachings may include at its distal end other electrically active components, such as a sensor for measuring characteristics of the environment proximate to the sensor, without departing from the scope of the present disclosure. Further still, the present disclosure is not limited to teleoperated surgical systems, and thus, an endoscope camera according to the present disclosure may not be attached to a camera arm as that shown in FIG. 2, but may be manually controlled.

In operation of a teleoperated surgical system as the ones described above, a surgical procedure may include making one or more incisions in a patient's body. Such incisions are sometimes referred to as "ports", a term which may also mean a piece of equipment that is used within such an incision. In some surgical procedures, several instrument and/or camera ports may be used to provide access to and imaging of a surgical site; however, in alternative embodiments, as described with reference to FIG. 2 for example, a single port may be used to introduce the various surgical and endoscope instruments.

Figure 3:
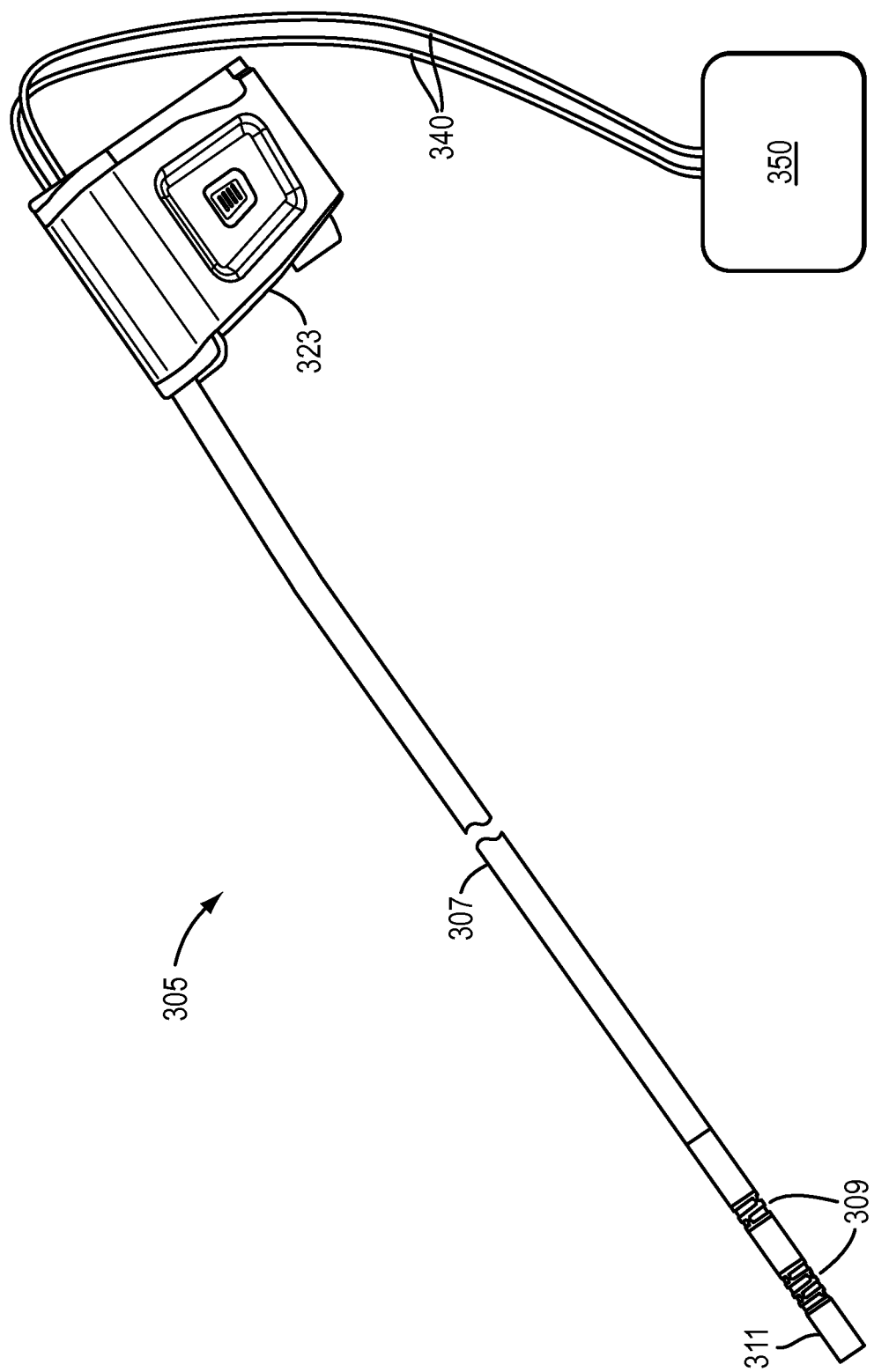
FIG. 3 is a diagrammatic view of an exemplary embodiment of an endoscopic image capture instrument for use with an endoscopic imaging system in accordance with the present disclosure.

Referring now to FIG. 3, an exemplary embodiment of an endoscopic image capture instrument for use with an endoscopic imaging system in accordance with the present disclosure is illustrated. The endoscopic image capture instrument 305 includes an endoscope shaft 307, a transmission housing 323 at the proximal end of the shaft 307, and an articulable wrist portion 309 at a distal portion of the shaft 307. As those having ordinary skill in the art are familiar with, the wrist portion 309 can be articulated via force transmission members (not shown) that extend along the shaft 307 from links of the wrist portion 309 to the transmission housing 323 where they are actuated (e.g., via modifying a force in the members) via actuators. In various exemplary embodiments, the actuators can be servo motors associated with the manipulation portion (e.g., ECM) of the arm of a patient side cart that are operative in response to master input commands provided at a surgeon console of a teleoperated surgical system. In the exemplary embodiment shown, the wrist portion 309 can be configured as a joggle joint wrist structure, as described for example in U.S. App. Pub. No. US 2011/0152879 A1, filed Jun. 23, 2011, which is incorporated by reference herein, although those having ordinary skill in the art would appreciate that a single articulated wrist component may be used or an endoscopic image capture instrument may not include a wrist structure at all. At the distal end 311 of the shaft 307, an image capture device (not shown) can be mounted inside the shaft 307.

In an exemplary embodiment, the image capture device is an electronic image sensor, such as for example a CMOS (complimentary metal-oxide semiconductor) or CCD (charge-coupled device) image sensor. As will be explained in further detail below, various signal processing and power transmission lines (e.g., cables) 340 can extend from the image capture device at the distal end 311 and along the shaft lumen so as to exit the proximal end of the endoscopic image capture instrument 305. Those lines 340 can be connected to a signal processor and a power supply, which may be separate or combined, and is depicted schematically as a combined module 350 in FIG. 3. In various exemplary embodiments, module 350 may be located at, for example, an electronics/auxiliary control cart or a patient side cart, such as electronics/auxiliary control cart 115, or the patient side cart 105, as respectively illustrated in FIG. 1, without departing from the scope of the present disclosure. The distal end 311, and thus image capture device, in the exemplary embodiment of FIG. 3 can be positioned by remotely controlling (e.g., through input commands at the surgeon console in a teleoperated surgical system or via manual actuation in a manual system) movement of the wrist portion 309.

As noted above, an electronic surgical instrument/device such as, for example, an endoscopic image capture instrument, may have one or more applied parts that come into contact with the patient during their normal operation and if not properly isolated could cause a current exceeding an allowable leakage current to flow to earth ground or through a conductive path of the surgical system. Accordingly, based on the nature of the instrument/device, and the type of contact the instrument/device may make with the patient, the surgical system associated with the control and operation of the instrument/device must be designed such that the instrument/device meets certain requirements for protecting against electrical shock of the patient (for example, CF rating or BF rating as per the IEC 60601-1 safety standard). As will be explained in detail below, endoscopic image capture, and other endoscopic instruments having electrically active components disposed at an applied part, according to exemplary embodiments of the present disclosure may be configured to meet or fall below electrical current leakage levels associated with the nature of the instrument/device and the type of contact the instrument/device may make with the patent.

Further as described above, during performance of a procedure at the remote surgical site, the endoscopic image capture instrument can be introduced at the site along with other surgical instruments for performing a variety of procedures. Often, the distal ends of the endoscopic image capture instrument and the surgical instrument(s) are in close proximity to permit viewing of the site while performing a surgical procedure. Some of the exemplary procedures performed may require the corresponding distal end (e.g. end effector) to receive electric current, as in, for example, an electrocautery procedure. This flow of current may generate electromagnetic interference (EMI) that may affect the operation of other instruments/devices, including the endoscopic camera instrument. For example, the flow of current may affect the various signal and power transmission lines that make up part of the image capture sensor system of the endoscopic image capture instrument, such as, for example, endoscopic image capture instrument 305 illustrated in FIG. 3. Furthermore, if the flow of current varies rapidly, as in alternating current for example, the flow of current may also generate differential interference among the various lines, which may exacerbate the degradation of the transmission of signals, both analog and digital, along the signal transmission lines of the endoscopic camera instrument.

As will be explained in detail below, exemplary embodiments according to present disclosure, therefore, provide a shielding configuration for an endoscopic image capture system or other endoscopic sensor system, that can protect against the negative effects of EMI generated by proximate surgical instruments such as, for example, an electrocautery instrument so as to reduce signal noise along the signal transmission lines.

Moreover, in various exemplary embodiments, endoscopic systems can meet desired electrical shock protection rating requirements while also protecting against the effects of EMI generated by proximate surgical instruments and/or other sources in the surrounding environment. Examples of potential EMI sources may include, but are not limited to, defibrillators and/or MRI imaging systems.

Figure 4:
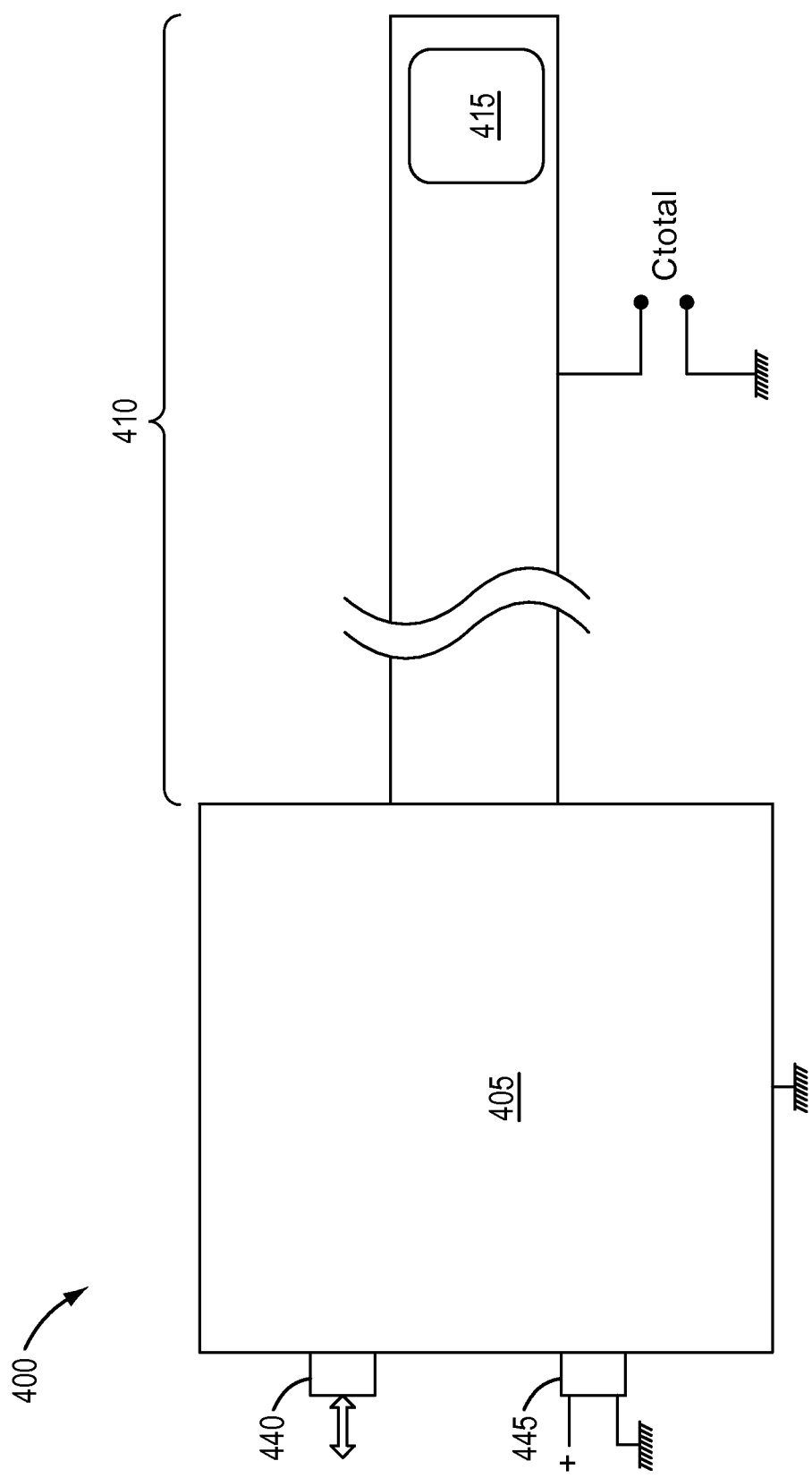
FIG. 4 schematically illustrates an endoscopic system according to various exemplary embodiments of the present disclosure.

FIG. 4 illustrates an endoscopic system 400 including a distally-positioned and electronic sensor for capturing information at a remote site according to various exemplary embodiments of the present disclosure. Endoscopic system 400 includes a grounded enclosure 405 that is coupled to an endoscope shaft 410, and an electronic sensor 415 at the distal end of the shaft 410. In various exemplary embodiments of the present disclosure, grounded enclosure 405 may be embodied within an element of the endoscopic system, such as module 350 or transmission housing 323 illustrated in FIG. 3, and/or may be integrated within one or more elements of a teleoperated surgical system such as teleoperated surgical system 100 illustrated in FIG. 1. For example, grounded enclosure 405 may be located at an electronics/auxiliary control cart or a patient side cart, such as electronics/auxiliary control cart 115 or patient side cart 105, as respectively illustrated in FIG. 1, without departing from the scope of the present disclosure.

Endoscopic system 400 further includes a communication interface 440 for communicating with external devices and/or systems such as, for example, processing and control components of a robotic surgical system, such as system 100 illustrated in FIG. 1. Endoscopic system 400 further includes a power interface 445 for supplying power to internal circuits and devices, including electronic sensor 415, within endoscopic system 400. In an exemplary embodiment, endoscopic system 400 may be an endoscopic image capture system and can include, for example, endoscopic camera instrument 305 illustrated in FIG. 3, for capturing images of a surgical site. In such an embodiment, electronic sensor 415 may be an electronic image sensor, such as for example, a CMOS image sensor. In an exemplary embodiment some or all of the elements of endoscopic system 400 may be mounted on a patient side manipulator arm, such as arm 120, 220 illustrated in FIGS. 1 and 2, respectively, of a robotic surgical system such as robotic surgical system 100 illustrated in FIG. 1.

In an exemplary embodiment of the present disclosure, at least a portion of endoscope shaft 410 may be inserted into a patient's body through, for example, one or more of an entry guide and a cannula, such as, for example, entry guide 208 and cannula 207 illustrated in FIG. 2. Electronic sensor 415 at the distal end of the endoscope shaft 410 may be embodied as an electronic image sensor, such as the image capture instrument described with respect to FIG. 3, to capture images of a surgical site. The sensor 415 may be powered by power received through power interface 445 via power transmission lines (not shown) extending along the shaft 410 to the sensor 415. During operation, control signals can be exchanged between a processor/controller, e.g., at the surgeon console 110, patient side cart 105 and/or the electronics/auxiliary control cart 115, logically coupled to the endoscopic system and the electronic sensor 415 through communication interface 440. This exchange, for example, can provide video and/or other captured images of the surgical site to the surgeon console or to control a function of the sensor device 415 such as, for example, zooming in/out of an electronic image sensor and/or to permit processing signal transmissions between the sensor 415 and video processing circuitry. In various exemplary embodiments of the present disclosure, the electronic image sensor may provide digital signals/data to the processor/controller representing images captured at the surgical site. However, the present disclosure is not so limited, and in various exemplary embodiments the electronic image sensor may provide analog signals to represent images captured at the surgical site without departing from the scope of the present disclosure.

Various exemplary embodiments of the present disclosure are configured such that a capacitance between applied parts of the endoscopic system 400 and earth ground is minimized, and may be minimized enough that at least some of the exemplary embodiments may achieve desired ratings for protection against electrical shock, such as, for example an IEC CF rating, which corresponds to about 500 pF when operating from a nominal 230 volts AC (with nominal encompassing 230 volts+\−10%), 60 Hz earth grounded power supply.

Further, when an endoscopic system such as endoscopic system 400 operates proximate to one or more surgical instruments that may generate EMI, operation of electronic sensor 415 and/or communication to and from electronic sensor 415 may be degraded by the generated EMI. For example, video signals transmitted from electronic sensor 415 that is an image sensor (either analog or digital) may be distorted by signal level changes induced by the generated EMI in a video signal transmission line (not shown) along the endoscope shaft 410. As will be described in detail below, exemplary embodiments of the present disclosure include a shielding configuration that can protect against the negative effects (e.g., noise) of external EMI in the operation of endoscopic system 400.

Further still, exemplary embodiments of the present disclosure can further minimize distortion caused by signal level changes induced by the generated EMI along a video signal transmission line (not shown) along the endoscope shaft by structuring the capacitance between the conductors along the endoscope (e.g., video signal transmission line, control signal transmission line, and power transmission line relative to a corresponding ground reference) (not shown) to be significantly larger than the capacitance between applied parts of the endoscopic system 400 and earth ground.

Endoscopic System with Low Capacitance

Figure 5:
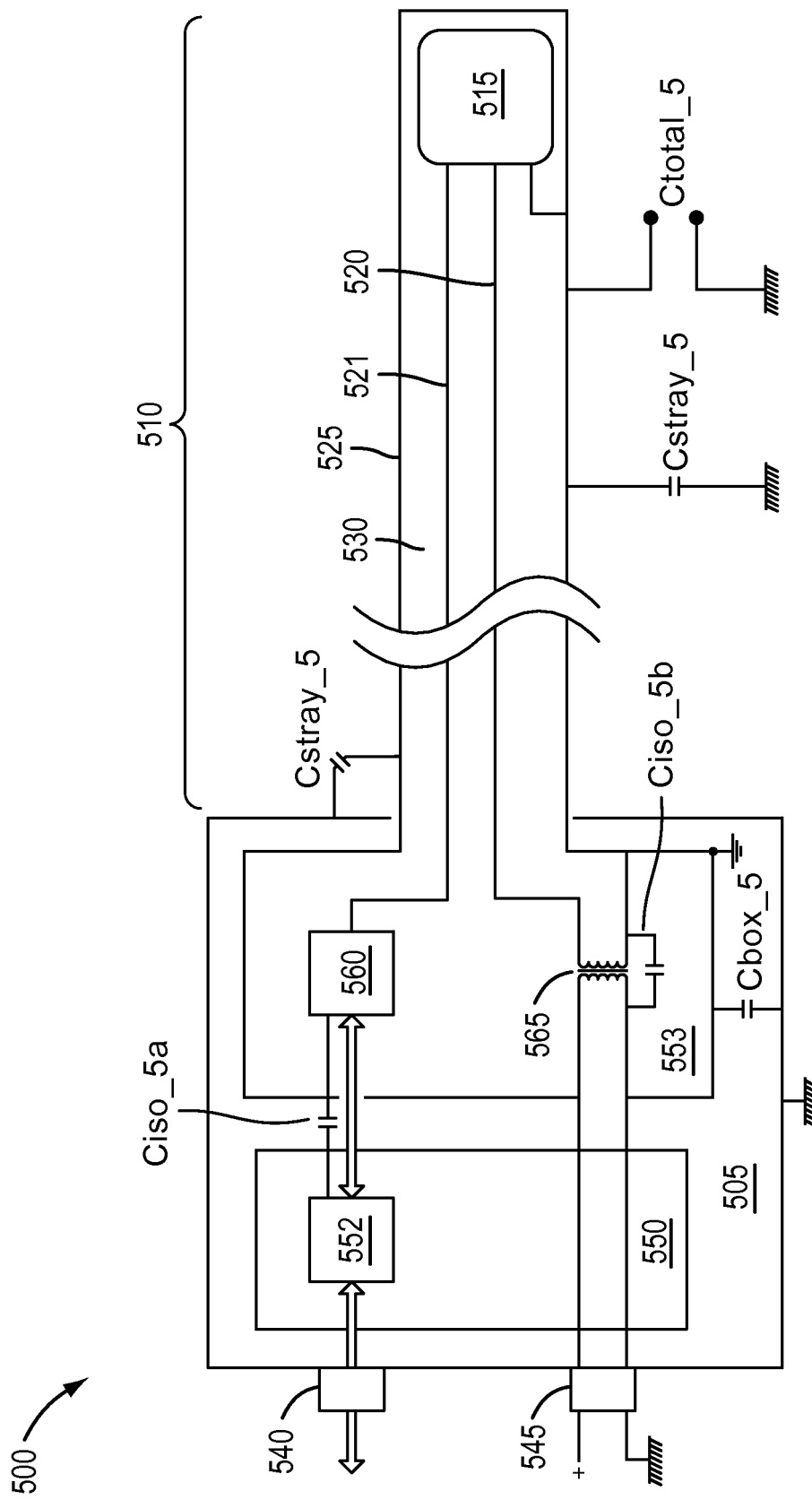
FIG. 5 schematically illustrates an endoscopic system according to various exemplary embodiments of the present disclosure.

FIG. 5 illustrates an endoscopic image capture system 500 that is configured to have relatively low capacitance and hence exhibiting relatively low leakage current according to various exemplary embodiments of the present disclosure. Endoscopic system 500 includes a grounded enclosure 505 that is coupled to an endoscope shaft 510, and an electronic image sensor 515 disposed at the distal end of the endoscope shaft 510. In an exemplary embodiment, endoscopic image capture system 500 can be mounted at a patient side manipulator arm, such as arm 120, 220 illustrated in FIGS. 1 and 2, respectively, of a robotic surgical system, such as robotic surgical system 100 illustrated in FIG. 1. Although FIG. 5 and the descriptions set forth below are directed to an endoscopic image capture system, the present disclosure is not so limited, and exemplary embodiments of the present disclosure may include other systems, such as ultrasonic endoscopic probes, endoscopic systems using pressure transducers (e.g., for measuring arterial blood pressure), endoscopic systems using electromagnetic sensors (e.g., for positioning and/or steering), endoscopic systems using temperature sensors, and/or endoscopic systems using chemical sensors (such as pH sensors), etc.

Endoscopic system 500 further includes power transmission line 520 for providing electric power to electronic image sensor 515, and output/control data transmission line 521 for exchanging output/control and video processing signals between electronic image sensor 515 and, for example, a surgeon console such as surgeon console 110 and/or electronics/auxiliary control cart 115 illustrated in FIG. 1 and logically coupled to endoscopic system 500 through communication interface 540.

Although power transmission line 520 is illustrated as a single line, the present disclosure is not so limited, and an exemplary embodiment may include one or more power transmission lines. For example, in various exemplary embodiments, electric power may be provided to electronic image sensor 515 through two power transmission lines which can include, for example, a relatively low voltage line (e.g., about 1.8 V) for powering logic circuitry in the electronic image sensor 515; and a relatively high voltage line (e.g., about 3.6 V) for powering the detection of analog pixels and amplifiers in the electronic image sensor 515.

Furthermore, although output/control data transmission line 521 is illustrated as a single line, the present disclosure is not so limited, and an exemplary embodiment may include separate lines for output data and control data, or multiple lines for each of output and control data. For example, in various exemplary embodiments, one line may be provided for the exchange of control data, and one or more lines may be provided for transmission of high-speed image data from the image sensor 515 to, for example, a surgeon console such as surgeon console 110 and/or electronics/auxiliary control cart 115 illustrated in FIG. 1. In one exemplary embodiment, output/control data transmission line 521 may include a twisted pair copper line.

Endoscopic system 500 further includes a floating ground 525, which surrounds transmission lines 520 and 521, and is separated from transmission lines 520 and 521 by an electrically insulative material 530. The material 530 may be selected based on desirable dielectric, flexibility, and strength properties. In an exemplary embodiment, the electrically insulative material 530 can include Ethylene tetrafluoroethylene (ETFE). However, exemplary embodiments of the present disclosure are not so limited, and the insulating material 530 may include a variety of electrically insulative materials. Other nonlimiting examples of suitable materials include silicone, polyvinyl chloride (PVC), and expanded polytetrafluoroethylene (ePTFE), without departing from the scope of the present disclosure.

Endoscopic system 500 further includes a communication interface 540 within grounded enclosure 505 for exchanging data with other elements of a teleoperated surgical system such as, for example, the electronics/auxiliary control cart 115 and surgeon console 110 illustrated in FIG. 1. Endoscopic system 500 further includes a power supply interface 545 within grounded enclosure 505 for providing external power from a power source (e.g., as in power source 350 in FIG. 3) to endoscopic system 500. Both communication interface 540 and power interface 545 can carry signals/electric power that is earth-grounded. However, the present disclosure is not so limited and communication interface 540 and power interface 545 may be grounded based on a non-earth-ground reference that is different from the floating ground reference 525 within endoscopic system 500.

Endoscopic system 500 further includes a processing circuit 550 within grounded enclosure 505 coupled to communication interface 540 for processing signals exchanged between communication interface 540 and electronic image sensor 515. However, exemplary embodiments of the present disclosure are not so limited, and some or all processing of signals may occur at, for example, other elements of a teleoperated surgical system such as, for example, the electronics/auxiliary control cart 115 and/or surgeon console 110 illustrated in FIG. 1.

Processing circuit 550 can include an optical transceiver circuit 552, as depicted in FIG. 5, for transforming electrical signals received at communication interface 540 into optical signals and vice versa. However, exemplary embodiments of the present disclosure are not so limited. For example, in various exemplary embodiments, the endoscopic system may exchange data with external elements, such as elements of an associated teleoperated surgical system, via optical signals, in which case, optical transceiver circuit 552 may be obviated.

Endoscopic system 500 further includes an optical transceiver circuit 560 and an isolated power supply 565. Optical transceiver circuit 560 is coupled to output/control transmission line 521 to exchange output/control electrical signals with electronic image sensor 515, and to optical transceiver circuit 552 of processing circuit 550 to exchange optical signals with optical transceiver circuit 552. The use of optical transceiver circuit 560 and an optical connection to provide signals to an associated teleoperated surgical system (either directly or through optical transceiver circuit 552 of processing circuit 550, which may be earth-grounded) isolates output/control transmission line 521 and electronic image sensor 515 (which are float-grounded) from earth-grounded elements. As will be explained in further detail below, this isolation may reduce leakage current from endoscope shaft 510 and/or electronic image sensor 515 to, for example, earth ground when these elements make contact with a patient.

Isolated power transformer 565 is coupled to receive earth-grounded power from power interface 545. Isolated power supply 565 is further coupled to power transmission line 520 and to floating ground 525. Isolated power transformer 565 transforms earth-grounded power received from power interface 545 into float-grounded power supplied to the electronic image sensor 515. In this way, the power interface 545, in communication with an external power source, is isolated from the power supply line of the transmission line 520 and from floating ground 525. Although endoscopic system 500 is shown as including isolated power transformer 565 supplied through power interface 545, the present disclosure is not so limited, and power may be supplied through a battery, either external or internal to endoscopic system 500, without departing from the scope of the present disclosure.

In an exemplary embodiment, as illustrated in FIG. 5, endoscopic system 500 may further include a circuit enclosure 553 coupled to the floating ground to provide EMI/induced voltage protection to optical transceiver circuit 560 and isolated power transformer 565. Circuit enclosure 553 may include, for example, a Faraday cage, which helps ensure that current generated by the EMI/induced voltage flows uniformly through the enclosure, minimizing or eliminating secondary interference in the circuits within. Specifically, in a condition in which the capacitance Cbox_5 is relatively large when compared to the capacitances Ciso_5a and Ciso_5b, interfering current is caused to flow through the box and not through the active circuitry.

In addition to the features set forth above, and other features that would be understood by a person having ordinary skill in the art, various exemplary embodiments of the present disclosure include elements to achieve a relatively low capacitance between the electronically active system components of the endoscopic system (e.g., electronic image sensor 515, transmission lines 520 and 521, and associated circuitry) and patient tissue (which may be earth-ground referenced). In an exemplary embodiment, the capacitance of the overall endoscopic system according to the present disclosure can be low enough to maintain current leakage from applied parts at levels that meet the requirements of at least a CF rating (which corresponds to about 500 pF, when operating from a nominal 230 Volts AC, 60 Hz earth grounded power supply), for example, in accordance with the standard set forth in IEC 60601-1. However, it should be understood by those having ordinary skill in the art that the present disclosure can be useful in achieving other electrical shock protection ratings for applied parts as desired depending on a particular application.

For example, the amount of leakage current is a function of the capacitance between the applied part and earth ground, illustrated as Ctotal_5 in FIG. 5. In various exemplary embodiments of the present disclosure, as in endoscope system 500, Ctotal_5 is, in significant part, the addition of Cstray_5 (stray capacitance of various elements of endoscopic system 500 relative to earth ground), Cbox_5 (capacitance between circuit enclosure 553 and earth ground), and Ciso_5 (capacitance between circuits within circuit enclosure 553 and earth ground; Ciso_5a for optical transceiver circuit 560 and Ciso_5b for isolated power transformer 565), as these capacitances are in parallel between elements/circuits of endoscopic camera 500 and earth ground. Thus, in various exemplary embodiments of the present disclosure, Ctotal_5 is kept low, in part by the use of a floating ground 525 for various circuits within endoscopic system 500 (e.g., electronic image sensor 515 and transmission lines 520 and 521), and by the isolation provided by the configuration of circuit enclosure 553 (Cbox_5); the optical connection optical transceiver circuit 560 that keeps internal signal data lines (float-grounded) isolated from external signal data lines (earth-grounded) (Ciso_5a); and the isolated power supply (Ciso_5b), which produces floating-ground power for the floating circuit.

In particular, with reference to FIG. 5, the capacitance between the floating-ground circuit and earth-ground includes Cstray_5 (stray capacitance between the applied part and earth ground), Ciso_5 (capacitance generated at interfaces between the floating circuit and the output/control signal interface (Ciso_5a) and between the floating circuit and the power interface (Ciso5b)), and Cbox_5 (capacitance between circuit enclosure 553 and grounded enclosure 505). With respect to Ciso_5, various embodiments of the present disclosure maintain a relatively low Ciso_5 by, for example, having an optical data communication link between the floating circuit within circuit enclosure 553 (transceiver circuit 560) and earth-ground signal transmission circuits (e.g., optical transceiver circuit 552) for exchanging output/control signals between electronic image sensor 515 and external elements such as, for example, a surgeon console (illustrated as Ciso_5a in FIG. 5). Ciso_5 can also be kept low by, for example, using an isolated power supply/regulator (illustrated as Ciso_5b in FIG. 5). With respect to Cbox_5, it may be kept low by building circuit enclosure 553 such that the capacitance between the circuit enclosure 553 and the grounded enclosure is low in ways known to those having ordinary skill in the art.

Endoscopic Electronic Sensor System with EMI Protection

Figure 6:
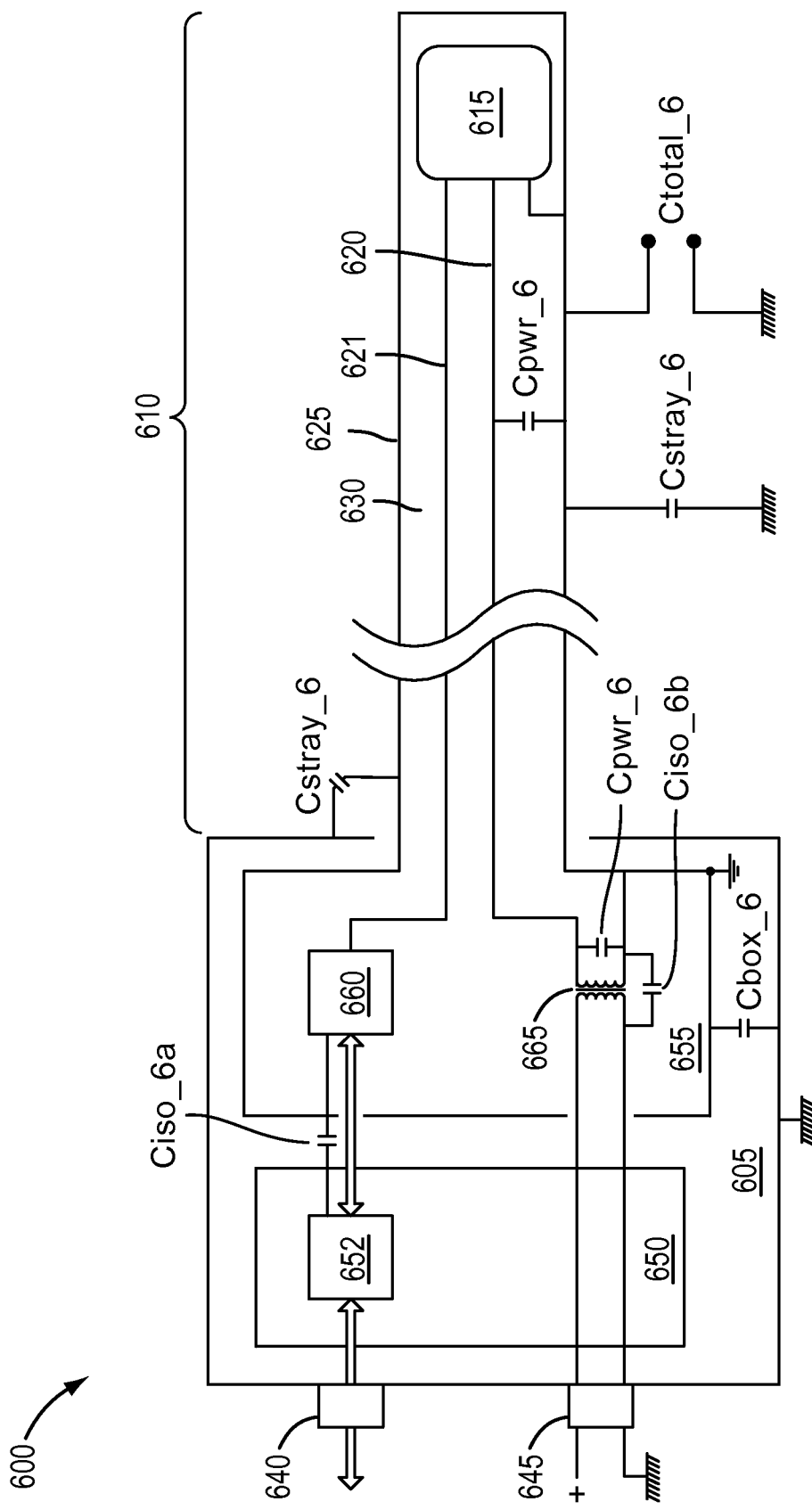
FIG. 6 schematically illustrates another endoscopic system according to various exemplary embodiments of the present disclosure.

FIG. 6 illustrates an endoscopic system 600 according to various exemplary embodiments of the present disclosure. Endoscopic system 600 includes a grounded enclosure 605 that is coupled to an endoscope shaft 610, and an electronic image sensor 615 disposed at the distal end of the endoscope shaft 610. In an exemplary embodiment, endoscopic image capture system 600 can be mounted at a patient side manipulator arm, such as arm 120, 220 illustrated in FIGS. 1 and 2, of a teleoperated surgical system, such as teleoperated surgical system 100 illustrated in FIG. 1. Although FIG. 6, and the descriptions set forth below, are directed to an endoscopic image capture system, the present disclosure is not so limited, and exemplary embodiments of the present disclosure may include other systems, such as ultrasonic endoscopic probes, endoscopic systems using pressure transducers (e.g., for measuring arterial blood pressure), endoscopic systems using electromagnetic sensors (e.g., for positioning and/or steering), endoscopic systems using temperature sensors, endoscopic systems using chemical sensors etc.

Endoscopic system 600 further includes power transmission line 620 and output/control data transmission line 621 along endoscope shaft 610 for providing electric power to electronic image sensor 615 and for exchanging output/control and video processing signals between electronic image sensor 615 and, for example, a surgeon console such as surgeon console 110 and/or electronics/auxiliary control cart 115 illustrated in FIG. 1 and logically coupled to endoscopic system 600 through communication interface 640. Although power transmission line 620 is illustrated as a single line, the present disclosure is not so limited, and an exemplary embodiment may include one or more power transmission lines. Furthermore, although output/control data transmission line 621 is illustrated as a single line, the present disclosure is not so limited, and an exemplary embodiment may include separate lines for output data and control data, or multiple lines for each of output and control data. Output/control data transmission line 621 may include a twisted pair copper line.

Endoscopic system 600 further includes a floating ground 625, which surrounds transmission lines 620 and 621, and is separated from transmission lines 620 and 621 by an electrically insulative material 630. The material 630 may be selected based on desirable dielectric, flexibility, and strength properties. In one exemplary embodiment, the electrically insulative material 630 can include Ethylene tetrafluoroethylene (ETFE). However, exemplary embodiments of the present disclosure are not so limited. Other suitable nonlimiting examples of electrically insulative materials can include silicone, polyvinyl chloride (PVC), and expanded polytetrafluoroethylene (ePTFE), without departing from the scope of the present disclosure.

Endoscopic system 600 further includes a communication interface 640 within grounded enclosure 605 for exchanging data with other elements of a teleoperated surgical system such as, for example, the electronics/auxiliary control cart 115 and surgeon console 110 illustrated in FIG. 1. Endoscopic system 600 further includes a power supply interface 645 within grounded enclosure 605 for providing external power from a power source (e.g., as in power source 350 in FIG. 3) to endoscopic system 600. Both communication interface 640 and power interface 645 are considered as carrying signals/electric power that is earth-grounded. However, the present disclosure is not so limited and communication interface 640 and power interface 645 may be grounded based on a non-earth-ground reference that is different from the floating ground reference 625 used within endoscopic system 600.

Endoscopic system 600 further includes a processing circuit 650 within grounded enclosure 605 coupled to communication interface 640 for processing signals exchanged between communication interface 640 and electronic image sensor 615. However, exemplary embodiments of the present disclosure are not so limited, and some or all processing of signals may occur in, for example, other elements of a teleoperated surgical system such as, for example, the electronics/auxiliary control cart 115 and surgeon console 110 illustrated in FIG. 1.

In various exemplary embodiments, endoscopic system 600 further includes a Faraday cage 655 within grounded enclosure 605 that is electrically coupled to floating ground 625 to shield enclosed elements from EMI (namely, transceiver circuit 660 and isolated power supply 665). Transceiver circuit 650 is coupled to output/control data transmission line 621 to exchange output/control electrical signals with electronic image sensor 615, and to optical transceiver circuit 652 of processing circuit 650 to exchange optical signals with transceiver circuit 652. The use of transceiver circuit 660 and a connection between transceiver circuit 660 (which is enclosed in Faraday cage 655) and transceiver circuit 652 of processing circuit 650 (which is outside Faraday cage 655 and may be earth-grounded) isolates transmission lines 620 and 621 and electronic image sensor 615 (which are float-grounded) from processing circuit 650 (which may be earth-grounded). It is noted, however, that exemplary embodiments of the present disclosure are not so limited. For example, in various exemplary embodiments, the endoscopic system may exchange data with external elements, such as elements of an associated teleoperated surgical system, via optical signals, in which case, optical transceiver circuit 652 may be obviated while maintaining a desired isolation without departing from the scope of the present disclosure. As will be explained in further detail below, this isolation may reduce the effect of EMI on output/control and video processing data signals along data signal lines within transmission lines 620 and 621.

Isolated power transformer 665 within Faraday cage 655 is coupled to receive earth-grounded power from power interface 645. Isolated power supply 665 is further coupled to power transmission line 620 and to floating ground 625. Isolated power transformer 665 transforms earth-grounded power received from power interface 645 into float-grounded power supplied to the electronic image sensor 615. In this way, the power interface 645, in communication with an external power source, is isolated from power transmission line 620 and from floating ground 625. Although endoscopic system 600 is shown as including isolated power transformer 665 supplied through power interface 645, the present disclosure is not so limited, and power may be supplied through a battery, either external or internal to endoscopic system 600, without departing from the scope of the present disclosure.

As above with reference to the description of FIG. 5, the amount of leakage current is a function of the capacitance between the applied part and earth ground, illustrated as Ctotal_6 in FIG. 6. Ctotal_6 is, in significant part, the addition of Cstray_6 (stray capacitance of various elements of the endoscope relative to earth ground), Cbox_6 (capacitance between Faraday cage 655 and earth ground), and Ciso_6 (capacitance between circuits within Faraday cage 655 and earth ground (Ciso_6a for transceiver circuit 660 and Ciso_6b for isolated power transformer 665)), as these capacitances are in parallel between elements/circuits of endoscopic camera 600 and earth ground. Thus, in various exemplary embodiments of the present disclosure, Ctotal_6 is reduced, in part, by the use of a floating-ground 625 as the electrical reference of various circuits within endoscopic system 600 and as isolation of the float-ground circuits provided by the configuration of the power transformer 655 (Ciso_6b). In exemplary embodiments, the floating ground 625 serves as the electrical reference for the sensor system that includes at least electronic image sensor 615, transmission lines 620 and 621, and Faraday cage 655 (which includes transceiver circuit 660 and isolated power transformer 665)).

In the exemplary embodiment illustrated in FIG. 6, isolated power transformer 665 provides a high capacitance (illustrated as Cpwr_6) relative to the capacitance between the floating circuit and earth ground illustrated as Ctotal_6 (i.e., Cpwr_6>>Ciso_6a+Ciso_6b+Cbox_6+Cstray_6). In an exemplary embodiment: Cpwr_6 is about 10 micro Farads (uF); Ciso_6a is about 10 pico Farads (pF); Ciso_6b is about 20 pF; Cbox_6 is about 100 pF; and Cstray_6 is about 50 pF, which yields a Cpwr_6 to Ctotal_6 ratio of about 55,000. However, the present disclosure is not so limited, and in various exemplary embodiments a Cpwr_6 to Ctotal_6 ratio may be higher than 55,000, and as low as about 10,000 or lower, without departing from the scope of the present disclosure. As will be explained below, this capacitance ratio minimizes the effects of EMI at least on output/control data transmission line 621.

Various exemplary embodiments of the present disclosure such as, for example, endoscopic system 600, include elements that may improve performance of the endoscopic system in the presence of EMI entering the endoscopic system from external sources such as, for example, cautery or other EMI-generating instruments being operated in close proximity to the endoscope shaft at the remote surgical site. In particular, various exemplary embodiments include elements to help to ensure that components, data transmission lines, and/or power transmission lines, are equally affected by any voltage level changes that might be induced by EMI.

For example, the above-referenced floating ground 625 is configured as a continuous shield around transmission lines 620 and 621, electronic image sensor 615, and faraday cage 655, and thus helps to ensure that the components it shields are approximately equally affected by any voltage level changes that might be induced by EMI. Furthermore, the relatively large ratio of Cpwr_6 to Ciso_6 (i.e., Cpwr_6>>Ciso_6a+Ciso_6b) also helps ensure that all shielded components are at nearly the same voltage in the presence of EMI.

Further still, a tight electromagnetic coupling of the transmission lines helps ensure that the voltage induced on the transmission lines is nearly equal. Ensuring that any voltage induced within components of the endoscopic system (e.g., electronic image sensor 615 and other components of that sensor system) is induced nearly equally onto the transmission lines particularly improves performance of the endoscopic system at least because interference introduced into the output/control signal data lines appear to optical transceiver circuit 660 as common-mode. Accordingly, signal level changes caused by EMI on the transmission lines remain low relative to the output/control signals, and thus, transmission/reception problems that could be caused by EMI are reduced.

In addition, the configuration of elements in various exemplary embodiments of the present disclosure, such as, for example, the configuration of endoscopic system 600 illustrated in FIG. 6, allows for a significant reduction (over conventional endoscopic systems) in the amount of current induced on floating ground 625 in the presence of high voltage interference, such as that which may be induced by electrocautery instruments operating in the proximity of the image sensor. For example, the capacitance between the floating ground and earth ground may be controlled across the frequency range covered by interfering signals. Specifically, in various exemplary embodiments of the present disclosure, Ctotal_6 is formed, in part, by the Faraday cage 655. The Faraday cage 655 and the floating ground shield 625 may be configured to form a high-frequency capacitor such that the Cbox_6 and Cstray_6 components of Ctotal_6 are well-controlled and free of resonances across a broad range of frequencies.

Furthermore, keeping capacitances illustrated in FIG. 6 as Cstray_6, Cbox_6, Ciso_6a, and Ciso_6b relatively low minimizes the generation of differential mode interference on output/control signals exchanged through transmission lines 620 and 621 through the mutual inductance coupling in the transmission lines. Any remaining differential mode interference may be obviated by using differential signaling to exchange output/control and processing signals along transmission lines 620 and 621, and/or by using a balanced/twisted pair of conductors for exchanging the output/control signals along endoscope shaft 610.

Thus, various exemplary embodiments of the present disclosure minimize and/or obviate the effects of EMI as a whole and/or across a broad range of frequencies on output/control signals exchanged between an electronic component, such as electronic image sensor 615 at the distal end of endoscopic shaft 610 and circuitry for controlling the endoscopic system and/or processing data associated with the endoscopic system.

Endoscopic System for Producing Low Leakage Current and EMI Protection

As noted above, various exemplary embodiments of the present disclosure, such as the exemplary embodiment illustrated in FIG. 5, may achieve an IEC 60601-1 safety standard CF rating (which, for operating from a nominal 230 Volts AC, 60 Hz earth grounded power supply, corresponds to about 500 pF). However, maintaining a low applied part-to-earth-ground capacitance (illustrated as Ctotal_5 in FIG. 5) may make an endoscopic system with an electrically active element, such as an endoscopic image sensor, vulnerable to EMI. In particular, EMI may induce voltage along conventional transmission lines that may increase errors in output/control signals exchanged along an endoscopic shaft between an endoscopic image sensor and, for example, a surgeon console. To counter the possible effects of EMI due to keeping a relatively low Ctotal_5, in various exemplary embodiments of the present disclosure EMI-induced voltage can be minimized by combining features of the various exemplary embodiments of the present disclosure which may achieve an IEC 60601-1 safety standard CF rating, such as the exemplary embodiment illustrated in FIG. 5, with features of the various exemplary embodiments which may improve performance of the endoscopic system in the presence of EMI, such as the exemplary embodiment illustrated in FIG. 6.

Figure 7:
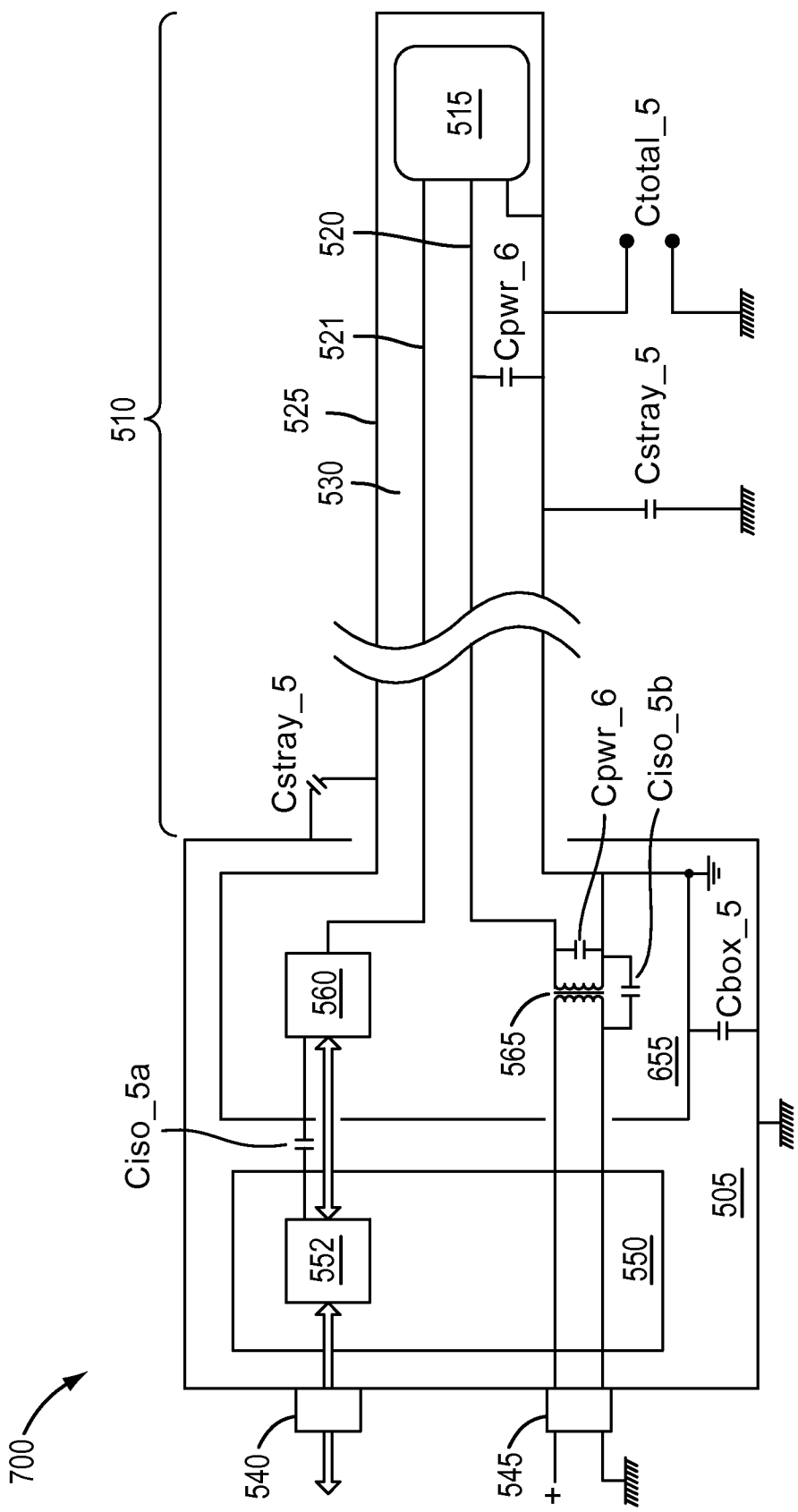
FIG. 7 schematically illustrates yet another endoscopic system according to various exemplary embodiments of the present disclosure.

FIG. 7 illustrates an exemplary embodiment according the present disclosure. For simplicity, FIG. 7 includes a plurality of elements already illustrated in, and described with reference to, FIG. 5 and FIG. 6. Those elements are identified in FIG. 7 according to their identifiers in their corresponding Figures, and their corresponding description is omitted here for brevity. At least the following features of the exemplary embodiment illustrated in FIG. 7 may realize an endoscopic electronic sensor system with relatively low capacitance to earth ground (so as to achieve relatively low leakage current and meet requirements for an electrical shock protection rating), while also providing EMI protection.

With respect to isolated power supply 565, which transforms earth-grounded power received from power interface 545 into floating grounded power for electronic image sensor 515, and with respect to endoscopic image sensor 515, various exemplary embodiments of the present disclosure are configured such that Cpwr_6>>Ciso_5, and also such that Cpwr_6>>Ciso_5+Cbox_5+Cstray_5. As explained above, this helps ensure that all shielded components, such as, for example, transmission lines 520 and 521, experience nearly the same level of induced voltage when in the presence of EMI. Accordingly, signal/power level changes caused by EMI on, for example, transmission lines 520 and 521 remain low relative to the output/control signals, which reduces transmission/reception problems that could otherwise be caused by EMI.

Furthermore, in various exemplary embodiments of the present disclosure, transmission lines 520 and 521 can be tightly coupled by, for example, being embodied in a balanced, twisted pair set of conductors. This helps ensure that transmission lines 520 and 521 are at nearly the same voltage in the presence of EMI which reduces transmission/reception problems that could otherwise be caused by EMI on transmission lines, as it helps a receiver better identify received signal data.

Further still, combining the tight coupling of the signal lines with differential signal transmission of output/control data signals, counters the effect of differential mode interference that may be caused by high voltage variations (dv/dt) proximal to the signal lines (such as, for example, the high dv/dt of electrocautery instruments), and thus, may further minimize transmission/reception problems conventionally caused by EMI on transmission lines.

Further still, the use of Faraday cage 655 to enclose optical transceiver circuit 560 and isolated power transformer 565 can provide some shielding of these components from the effects of EMI. In addition the use of floating ground 525 as a continuous shield further helps to ensure that the components it shields (e.g., transmission lines 520 and 521, optical transceiver circuit 560, and isolated power transmission 565) are approximately equally affected by any voltage level changes that might be induced by EMI external to the endoscopic system.

Further still, the capacitance between the floating ground and earth ground may be controlled across the frequency range covered by interfering signals. Specifically, in various exemplary embodiments of the present disclosure, Ctotal_5 is formed, in part, by the Faraday cage 655. The Faraday cage 655 and the floating ground shield 525 may be configured to form a high-frequency capacitor such that the Cbox_5 and Cstray_5 components of Ctotal_5 are well-controlled and free of resonances across a broad range of frequencies.

Therefore, various exemplary embodiments of the present disclosure maintain a low capacitance from an endoscopic system's applied part to earth-ground. Furthermore, various exemplary embodiments of the present disclosure minimize the effects of voltages induced by EMI into, for example, transmission lines along an associated endoscopic shaft. Further still, various exemplary embodiments of the present disclosure maintain a low capacitance from an endoscopic system's applied part to earth-ground while minimizing the effects of voltages induced by EMI.

Although the exemplary embodiments and descriptions above focus mainly on an endoscopic system including an endoscopic image capture system for performing remotely-controlled surgical applications, a person having ordinary skill in the art would recognize that the present disclosure is not limited, and the principles of the present disclosure could be applied in other endoscopic systems, such as, for example, sensor systems for capturing and providing one or more characteristics of a surgical site, without departing from the scope of the present disclosure. Moreover, with respect to the terminology "surgical procedure," "surgical site," and variations thereof, those having ordinary skill in the art will appreciate that the present teachings also apply to non-surgical procedures performed at remote sites, such as, for example, various diagnostic and/or therapeutic procedures; therefore the term "surgical" should be construed broadly to encompass any procedure in which an instrument is inserted through the patient's body to a remote location within the body to perform a surgical, diagnostic, and/or therapeutic procedure.

Other embodiments of the invention will be apparent to those having ordinary skill in the art from consideration of the specification and practice of the present disclosure and claims herein. It is intended that the specification and examples be considered as exemplary only, with a true scope and spirit of the invention being indicated by the following claims.

What is claimed is:

1. An endoscopic system comprising:
   an endoscope shaft having a proximal end and a distal end;
   an electrically active sensor system comprising:
      a sensor mounted proximate the distal end and positioned to sense at least one characteristic of an environment in which the distal end is located,
      a transceiver circuit coupled to the sensor,
      a data signal transmission line connected to the sensor to transmit data signals between the sensor and a signal processor, via the transceiver circuit, and
      an electrical power transmission line connected to the sensor to transmit power from a power source to the sensor;
   a floating ground element coupled to provide an electrical reference for the sensor system, wherein the floating ground element comprises a conductive material surrounding the data signal transmission line and the electrical power transmission line; and
   a power regulator coupled between the electrical power transmission line and the floating ground element, the power regulator to provide electrical power to the sensor system, wherein the power regulator converts ground-referenced power received from an earth ground referenced power source into floating ground element referenced power and outputs the floating ground element referenced power through the electrical power transmission line,
   wherein:
      the transceiver circuit isolates the sensor from earth grounded elements communicating with the sensor,
      an overall capacitance between the electrical power transmission line and the floating ground element is larger than an overall capacitance between the floating ground element and earth ground, and
      a capacitance of the sensor system relative to earth ground maintains current leakage from one or more applied parts of the endoscopic system to a patient to a predetermined current leakage criteria.

2. The endoscopic system of claim 1, further comprising an electrically insulative material separating the floating ground element from each of the data signal and electrical power transmission lines.

3. The endoscopic system of claim 1, wherein the data signal transmission line is configured to transmit data signals via a differential mode.

4. The endoscopic system of claim 3, wherein the differential mode is a differential digital mode.

5. The endoscopic system of claim 1, wherein:
   the transceiver circuit comprises an optical transceiver connected to the data signal transmission line and to an optical interface,
   the optical transceiver receives input electronic signals from the data signal transmission line and outputs corresponding output optical signals through the optical interface, and
   the optical transceiver receives input optical signals through the optical interface and outputs corresponding output electronic signals through the data signal transmission line.

6. The endoscopic system of claim 5, further comprising:
   a Faraday cage coupled to the floating ground element and enclosing the optical transceiver and the power regulator.

7. The endoscopic system of claim 6, further comprising:
   a data interface;
   a second optical transceiver coupled to the optical transceiver to exchange optical signals with the optical transceiver and coupled to the data interface to exchange electrical signals through the data interface; and
   an earth ground-referenced power interface to receive earth ground-referenced power from the earth ground-referenced power source.

8. The endoscopic system of claim 7, wherein:
   the sensor system transmits sensor data through the data signal transmission line by a differential mode.

9. The endoscopic system of claim 8, wherein:
   the differential mode is a differential digital mode.

10. The endoscopic system of claim 1, wherein the capacitance of the sensor system relative to earth ground is less than 500 pF under a condition of an earth ground referenced power source providing a nominal 230 volts under alternating current at 60 Hertz.

11. The endoscopic system of claim 1, wherein the sensor is an electronic image sensor.

12. The system of claim 1, wherein,
   a ratio of the capacitance between the electrical power transmission line and the floating ground element to the capacitance between the floating ground element and earth ground is in a range of from 10,000 to 1 to 55,000 to 1.

13. A method for sensing information at a remote surgical site via an endoscopic system, the method comprising:
   at a remote surgical site, sensing a characteristic of the remote surgical site via a sensor disposed proximate a distal end of an endoscope shaft;
   during the sensing, transmitting power to the sensor, via a power transmission line and a power regulator, from a ground-referenced power source;
   during the sensing, transmitting data signals to the sensor via a data signal transmission line from a processing circuit at a proximate end of the endoscopic shaft, wherein the processing circuit is isolated from the data signal transmission line by a transceiver circuit disposed between the data signal transmission line and the processing circuit;

in response to electromagnetic interference proximate to the remote surgical site, causing, at least in part by a floating ground element arranged to provide an electrical reference for the sensor, induced voltage level changes in the data signal transmission line and the power transmission line to be substantially equalized, wherein an overall capacitance between the power transmission line and the floating ground element is larger than an overall capacitance between the floating ground element and earth ground; and maintaining current leakage, from one or more applied parts of the endoscopic system to a patient, to a level that meets a predetermined current leakage criteria, wherein the current leakage is maintained using the floating ground element and the transceiver circuit.

14. The method of claim 13, wherein the remote surgical site comprises a cardiothoracic cavity.

15. The method of claim 13, wherein the remote surgical site comprises a heart.

16. An endoscopic system comprising:
a sensor mounted proximate a distal end of an endoscopic shaft and positioned to sense at least one characteristic of an environment in which the distal end is located;
a data signal transmission line connected to the sensor to transmit data signals between the sensor and a signal processor, via a transceiver circuit, wherein the transceiver circuit isolates the sensor from earth grounded elements communicating with the sensor;
a floating ground element coupled to provide an electrical reference for the sensor; and
an electrical power transmission line connected to the sensor to transmit power to the sensor, wherein the electrical power transmission line transmits power from a power regulator that converts ground-referenced power received from an earth ground referenced power source into floating ground element referenced power, wherein:
an overall capacitance between the electrical power transmission line and the floating ground element is larger than an overall capacitance between the floating ground element and earth ground, and
a capacitance of the endoscopic system relative to earth ground maintains current leakage from one or more applied parts of the endoscopic system to a patient within a predetermined current leakage threshold.

17. The endoscopic system of claim 16, wherein:
the sensor is configured to transmit sensor data through the data signal transmission line by a differential mode.

18. The endoscopic system of claim 16, wherein,
a ratio of the capacitance between the electrical power transmission line and the floating ground element to the capacitance between the floating ground element and earth ground is in a range of from 10,000 to 1 to 55,000 to 1.

19. The endoscopic system of claim 16, wherein:
the transceiver circuit comprises an optical transceiver electrically coupled to the data signal transmission line and to an optical interface.

20. The endoscopic system of claim 16, wherein the capacitance of the endoscopic system relative to earth ground is less than 500 pF under a condition of an earth ground referenced power source providing a nominal 230 volts under alternating current at 60 Hertz.

* * * * *

UNITED STATES PATENT AND TRADEMARK OFFICE
CERTIFICATE OF CORRECTION

| | | |
|---|---|---|
| PATENT NO. | : 11,284,803 B2 | |
| APPLICATION NO. | : 14/080384 | |
| DATED | : March 29, 2022 | |
| INVENTOR(S) | : Dominique Brichard et al. | |

It is certified that error appears in the above-identified patent and that said Letters Patent is hereby corrected as shown below:

In the Claims

Column 23, Line 11, Claim 13: delete "substantially".

Signed and Sealed this
Sixth Day of September, 2022

Katherine Kelly Vidal
*Director of the United States Patent and Trademark Office*